(12) United States Patent
Nehme et al.

(10) Patent No.: US 6,387,950 B2
(45) Date of Patent: May 14, 2002

(54) TREATMENT OF TUMORS WITH RARα SELECTIVE RETINOID COMPOUNDS IN COMBINATION WITH OTHER ANTI-TUMOR AGENTS

(75) Inventors: Alissar Nehme; Richard L. Beard, both of Newport Beach; Roshantha A. Chandraratna, Laguna Hills, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/824,111

(22) Filed: Apr. 2, 2001

Related U.S. Application Data (63) Continuation-in-part of application No. 09/542,148, filed on Apr. 4, 2000, now abandoned.
(51) Int. Cl.⁷ .............................................. A61K 31/45
(52) U.S. Cl. ...................... 514/539; 514/563; 560/45; 562/455
(58) Field of Search ................................ 514/539, 563; 560/45; 562/455

(56) References Cited

U.S. PATENT DOCUMENTS 5,856,490 A  1/1999  Teng et al.

FOREIGN PATENT DOCUMENTS

| WO | WO9311755 | 6/1993 |
| WO | WO9724116 | 7/1997 |

OTHER PUBLICATIONS

Schapira et al., Proc. Nat'l Acad. Sci. 97 No. 3 Feb. 1, 2000, pp. 1008–1013.
Teng et al, J. Med. Chem. 39 No. 16, 1996, pp. 3035–3038.
Fanjul et al., Cancer Research 56, pp. 1571–1577 (1996).
Toma et al., International Journal of Oncology 10, pp. 597–607 (1997).
Kurbacher et al., Cancer Letters 103 (1996), pp. 183–189.

*Primary Examiner*—James H. Reamer
(74) *Attorney, Agent, or Firm*—Gabor L. Szekeres; Carlos A. Fisher; Robert J. Baran (57) ABSTRACT

Compounds which are specific or selective agonists of RARα receptors in preference over RARβ and RARγ receptors, and particularly compounds of the formula

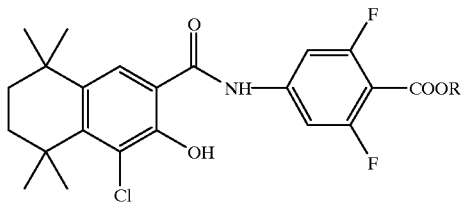

where R is a H, lower alkyl of 1 to 6 carbons, or a pharmaceutically acceptable salt, are useful for treating a malignant disease or condition in a mammal. In treatment of solid tumors the compound exhibit synergistic anti-proliferative effect with human recombinant interferon.

28 Claims, 8 Drawing Sheets

_FIG. 9._

_FIG. 10._

TREATMENT OF TUMORS WITH RARα SELECTIVE RETINOID COMPOUNDS IN COMBINATION WITH OTHER ANTI-TUMOR AGENTS

This application is a continuation-in-part of application Ser. No. 09/542,148 filed Apr. 4, 2000 now abandoned.

BACKGROUND OF THE INVENTION

1. Field of the Invention

The present invention relates to the use of RARα specific or selective retinoid compounds in combination with interferons and other anti-tumor agents. More particularly the present invention relates to the use of RARα specific or selective retinoid compounds for the treatment of carcinoma of the breast in combination with interferons and other anti-tumor agents. Still more particularly, the present invention relates to the use of 4-[(4-chloro-3-hydroxy-5,5,8,8-tetramethyl-5,6,7,8-tetrahydro-naphthalene-2-carbonyl)-amino]-2,6-difluoro-benzoic acid and related compounds in combination with interferons and other anti-tumor agents, and specifically to the use of 4-[(4-chloro-3-hydroxy-5,5,8,8-tetramethyl-5,6,7,8-tetrahydro-naphthalene-2-carbonyl)-amino]-2,6-difluoro-benzoic acid and related compounds for the treatment of carcinoma of the breast in combination with interferons and other anti-tumor agents.

2. Background Art

Naturally occurring retinoic acid and related compounds, generally called retinoids, have been known in the biopharmaceutical, medical and related arts to have of important biological activity, including prevention and inhibition of malignant cell proliferation. A vast volume of patent and scientific literature exists describing the synthesis of retinoid compounds, their biological activities and investigations aimed at discovering the varying modes of action of retinoids in human and and other biological systems, *in vitro* and *in vivo* as well.

Specifically, it is generally accepted in the art that in the anti-cell-proliferative or anti-tumor field, pharmaceutical compositions having a retinoid-like compound or compounds as the active ingredient are useful for treating or preventing hyperproliferative disorders of the skin, and other premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. However, a generally recognized disadvantage of treatment of mammals by retinoids is their mucocutaneous toxicity which occurs in greater than 90% of patients when treated with an effective dose of retinoids, topically or systemically.

It is now also general knowledge in the art that two main types of retinoid receptors exist in mammals (and other organisms). The two main types or families of receptors are respectively designated the RARs and RXRs. Within each type there are subtypes; in the RAR family the subtypes are designated RARα, RARβ and RARγ, in RXR the subtypes are: RXRα, RXRβ and RXRγ. It has also been established in the art that the distribution of the two main retinoid receptor types, and of the several sub-types is not uniform in the various tissues and organs of mammalian organisms. Moreover, it is generally accepted in the art that many unwanted side effects of retinoids, such as the mucocutaneous toxicity are mediated by one or more of the RAR receptor subtypes. A publication by *Standeven et al.,* Toxicology Letters 92 (1997) 231–240 discloses that treatment of mice by RARα selective retinoids results in significantly reduced skin irritation (mucocutaneous toxicity) than treatment with retinoids which have strong RARβ and particularly RARγ agonist activity.

U.S. Pat. No. 5,965,606 discloses methods of treatment of tumors with RARα specific or selective retinoids, and the synthesis of such retinoids is described in this patent as well as in U.S. Pat. No. 5,856,490. An important RARα selective compound of U.S. Pat. No. 5,965,606 (Compound 32 of this patent reference) is shown below.

With regard to using retinoids in combination with other drugs to treat tumors, there are published reports in the art that certain retinoid compounds act additively and some even synergistically with other known anti-tumor chemotherapeutic agents, such as interferons and other drugs, in several carcinoma of the breast cell cultures to suppress or inhibit the proliferation of the cancer cells. The publication by *Fanjul et al.* in Cancer Research 56, 1571–1577 (1996) describes assays of several retinoid compounds, including a compound designated in the publication as SRI 11220 in combination with interferon in several carcinoma cell lines, and states that in some of the cell lines the anti-proliferative activity of the compound SRI 11220 and interferon was synergistic. The structure of this prior art compound SRI 11220 is shown below. Significantly however, the *Fanjul et al.* reference attributes the inhibition of breast cancer cells by selective retinoids and interferon to the potential role of the RARγ receptors. In fact, the compound SRI 11220 is disclosed in this reference as an RARγ agonist.

Prior Art

Compound 32 of U.S. Pat. No. 5,965,606
Compound 36 of U.S. Pat. No. 5,856,490

SRI 11220 (Prior Art)

A publication by *Toma et al.* in International Journal of Oncology 10: 597–607 (1997) describes synergistic effects of certain other retinoids, such as all trans retinoic acid (tRA) with α interferon (α IFN) and synergistic effect with other chemotherapeutic agents such as tamoxifen (TAM) in MCF-7 human breast cancer lines. As further background to the present invention it is noted that a publication by *Kurbacher et al.* in Cancer Letters 103 (1996) 183–189 describes synergistic action of vitamin C with certain chemotherapeutic anti-tumor agents in MCF-7 and MDA-MB 231 human carcinoma cell lines.

U.S. Pat. No. 5,856,490 discloses aryl or heteroarylamides of tetrahydronaphthalenes, which are generally speak- ing RARα specific retinoids. Among the compounds specifically described as preferred embodiments in that reference is the 2,6-difluoro-4-[3'-hydroxy-4'-bromo-5',6',7',8'-tetrahydro-5'5',8',8'-tetramethylnaphthalen-2'-yl) carbamoyl]benzoic acid, the structure of which is shown above. In the U.S. Pat. No. 5,856,490 reference this compound is designated compound 36.

SUMMARY OF THE INVENTION

The present invention relates to the use of RARα specific or selective retinoids in combination with other anti-tumor agents for the treatment of a malignant tumor or condition in a mammal in need of such treatment. The RARα specific or selective retinoid is generally speaking administered to the mammal in need of such treatment in a pharmaceutical composition comprising a pharmaceutically acceptable excipient and the RARα specific or selective retinoid as the active ingredient. The other anti-tumor agent of the combination therapy may be administered in the same or in a different pharmaceutical composition.

The present invention also relates to compounds of Formula 1

FORMULA 1

R = H or lower alkyl of 1 to 6 carbons where R represents H or a lower alkyl group having 1 to 6 carbons, and to pharmaceutically acceptable salts of said compounds, and to the use of compounds of Formula 1 in combination with other anti-tumor agents for the treatment of a malignant tumor or condition in a mammal in need of such treatment. Furthermore, the present invention also relates to a pharmaceutical composition for treatment of a malignant tumor or condition in a mammal in need of such treatment, where the active ingredient of the composition comprises one or more compounds of Formula 1. Such pharmaceutical composition comprising as its active ingredient one or more compounds of Formula 1 is advantageously used in combination with one or more other anti-tumor agents for the treatment of a malignant tumor or condition in a mammal in need of such treatment.

RARα Specific or Selective Compounds used in the Invention, Assays to Establish Selectivity RARα specific and or RARα selective compounds can be obtained, for example, as described in U.S. Pat. Nos. 5,856,490 and 5,965,606, the specifications of which are expressly incorporated herein by reference. These references also present data to show that the compounds are indeed RARα specific or selective agonists. Assays by which a compound can be tested and established whether or not it is an RARα specific or selective agonist, are known in the art and are described in numerous prior art publications and patents. For example, a chimeric receptor transactivation assay which tests for agonist-like activity in the RAR$_α$, RAR$_β$, RAR$_γ$, RXR$_α$ receptor subtypes, and which is based on work published by *Feigner P. L. and Holm M.* (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the ligand binding assay is also provided below.

Ligand Binding Assay

All binding assays were performed in a similar fashion. All six receptor types were derived from the expressed receptor type (RAR α, β, γ and RXR α, β, γ) expressed in Baculovirus. Stock solutions of all compounds were prepared as 10 mM ethanol solutions and serial dilutions carried out into 1:1 DMSO; ethanol. Assay buffers consisted of the following for all six receptor assays: 8% glycerol. 120 mM KCl. 8 mM Tris. 5 mM CHAPS 4 mM DTT and 0.24 mM PMSF. pH-7.4@room temperature.

All receptor biding assays were performed in the same manner. The final assay volume was 250 μl and contained from 10–40 μg of extract protein depending on receptor being assayed along with 5 nM of [$^3$H] all-trans retinoic acid or 10 nM [$^3$H] 9-cis retinoic acid and varying concentrations of competing ligand at concentrations that ranged from 0–$10^{-5}$M. The assays were formatted for a 96 well minitube system. Incubations were carried out at 4° C. until equilibrium was achieved. Non-specific binding was defined as that binding remaining in the presence of 1000 nM of the appropriate unlabeled retinoic acid isomer. At the end of the incubation period. 50 μl of 6.25% hydroxyapitite was added in the appropriate wash buffer. The wash buffer consisted of 100 mM KCl. 10 mM Tris and either 5 mM CHAPS (RXR α, β, γ) or 0.5% Triton X-100 (RAR α, β, γ). The mixture was vortexed and incubated for 10 minutes at 4° C., centrifuged and the supernatant removed. The hydroxyapitite was washed three more times with the appropriate wash buffer. The receptor-ligand complex was adsorbed by the hydroxyapitite. The amount of receptor-ligand complex was determined by liquid scintillation counting of hydroxyapitite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a loglogit plot of the data. The $K_d$ values were determined by application of the Cheng-Prussof equation to the $IC_{50}$ values, the labeled ligand concentration and the $K_d$ of the labeled ligand.

The results of ligand binding assay are expressed in $K_d$ numbers. (See *Cheng et al.* Biochemical Pharmacology Vol. 22 pp 3099–3108, expressly incorporated herein by reference.)

A detailed experimental procedure for holoreceptor transactivations has been described by *Heyman et al.* Cell 68, 397–406, (1992); *Allegretto et al.* J. Biol. Chem. 268, 26625–26633, and *Mangelsdorf et al.* The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay.

In the chimeric transactivation assay Compound 2 of the present disclosure was found to have an $EC_{50}$ value of 180 nanomolar witith 75% efficiency at the RARα receptors, and in the ligand binding assay a $K_d$ value of 5 nmolar. For RARβ and RARγ receptors Compound 2 was found to be inactive as an agonist, with an $EC_{50}$ values greater than $10^4$ nanomolar.

Still another transactivation assay, the "PGR assay" is described in the publication *Klein et al.* J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR Holoreceptor Transactivation Assay

CV-1 cells ($4 \times 10^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation *Chen et al.* (1987) Mol. Cell. Biol. 7, 2745–2752 as described by *Klein et al.* in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in *de Wet* (1987) Mol. Cell. Biol. 7, 725–737. Luciferase values represent the mean±SEM of triplicate determinations normalized to β-galactosidase activity.

Preferred RARα Selective Agonist Compounds Used in the Invention

Presently preferred RARα specific or selective compounds of the invention are those disclosed in U.S. Pat. No. 5,965,606. The most preferred RARα specific or selective compounds of the invention are shown in Formula 1. These compounds also represent new composition of matter and are considered novel and inventive *per se*. Preferred embodiments of the compounds of the invention within the scope of Formula 1 are those where the R group of Formula 1 is H or lower alkyl of 1 to 3 carbons, or a pharmaceutically acceptable salt thereof. The most preferred compound of the invention is where the R group is H, or a pharmaceutically acceptable salt of said compound. In this connection its noted that a pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Generally speaking, the compounds of Formula 1 can be obtained by the synthetic procedures described in U.S. Pat.

No. 5,856,490, expressly incorporated by reference. A presently preferred synthetic process for the preparation of the preferred compound of the invention where R is H, and of the corresponding ethyl ester is described in detail below.

Anti-proliferative Effects of the Compounds of the Invention

The anti-proliferative effects of the compounds of the invention are demonstrated by assay procedures well accepted in the art. These assays are performed on the preferred compound of the invention, Compound 2, also named AGN 195183 without and in combination with human recombinant α, β and γ interferon which are anti-tumor agents well known in the art. (The AGN number is a number arbitrarily assigned to compounds in the research laboratories of the assignee of the present invention.) The materials and the assays procedures are described in detail below.

The SKBR-3 and T47-D cell cultures in which the assay procedures were performed are also well known and are available from sources well known in the art. Specifically, as is known, T-47D is an estrogen receptor positive ($ER^+$) human breast cancer cell line, and SK-BR-3 is an estrogen receptor negative ($ER^-$) human breast cancer cell line. The assay procedure which itself is well known in the art, involves determining incorporation of 5-bromo-2'-deoxyuridine (BrdU) into the cells. As is known, incorporation of less BrdU represents less cell proliferation (inhibition of cell proliferation), and this assay is accepted in the art as a measure of anti-proliferative or anti-tumor activity of the assayed agent or agents.

When a combination of two or more anti-proliferative or potentially anti-proliferative agents is assayed, the results may indicate less inhibition of proliferation than what we would be expected if the effects of the individual agents were additive, or the effects may represent the mathematical product of the expected effects of the two agents (additive inhibition). Alternatively, the inhibition actually observed experimentally may be greater than what would be expected as a simple product of the effects of the two agents. Such synergistic anti-tumor or antiproliferative effect is highly desirable, and as is described below was observed in several assays when Compound 2 of the invention was used in combination with human recombinant interferon. This synergistic effect of the compounds with interferon in the treatment of tumors, and especially of breast cancer, is not expected based on the prior art and is unobvious and surprising. The materials and procedures of the assays as well as the mathematical criteria for determining synergistic effects are described below.

Materials, Assay Methods and Criteria for Determining Synergism Reagents The human recombinant interferon-alpha (IFN-α) and human recombinant interferon-beta (IFN-β) were purchased from Sigma Chemicals Co. (St Louis, Mo.). Human recombinant interferon-gamma (IFN-γ) was purchased from Roche Diagnostics (Indianapolis, Ind.). The stock solutions were stored at −70, 4, and −20° C. for IFN-α, IFN-β and IFN-γ, respectively. IFN working solutions were prepared before use by dilutions in the culture medium. 5 mM stock solution for Compound 2 (AGN195183) was prepared in DMSO, which was subsequently diluted in culture medium to the indicated final concentration.

Synthesis of Preferred Compounds (Reaction Scheme 1)

-continued

Compound 1

Compound 2

Methyl 2,6-difluoro-4-[(3-methoxymethoxy-5,5,8,8-tetramethyl-5,6,7,8-tetrahydro-naphthalene-2-carbonyl)-amino]-benzoate (Compound A)

To a solution of 3-methoxymethoxy-5,5,8,8,-tetramethyl-5,6,7,8-tetrahydro-naphthalene-2-carboxylic acid (Compound K, as described in U.S. Pat. No. 5,856,490, 112mg, 0.38 mmol) in 6 ml of anhydrous methylene chloride was added 4-(dimethylamino)pyridine (DMAP, 100 mg, 0.46mmol), methyl 2,6-difluoro-4-aminobenzoate (Compound H1, as described in U.S. Pat. No. 5,856,490, 77mg, 0.38mmol ) and 1-(3-dimethylaminopropyl)-3-ethylcarbodiimide hydrochloride (EDC, 110 mg, 0.57 mmol). The reaction mixture was stirred at room temperature for overnight then concentrated to dryness. The residue was purified by column chromatography with ethyl acetate: hexane (1:9) to yield the title compound as a clear oil.

$^1$H NMR CDCl$_3$ δ 8.18 (s, 1H), 7.38 (s, 1H), 7.35 (s, 1H), 7.10 (s, 1H), 5.39 (s, 2H), 3.94 (s, 3H), 3.59 (s, 3H), 1.70 (s, 4H), 1.31 (s, 3H), 1.30 (s, 3H).

2,6-difluoro-4-[(3-hydroxy-5,5,8,8,-tetramethyl-5,6,7,8-tetrahydronaphthalene-2-carbonyl) -amino]-benzoic acid (Compound B)

A solution of methyl 2,6-difluoro-4-[(3-methoxymethoxy-5,5,8,8,-tetramethyl-5,6,7,8-tetrahydro-naphthalene-2-carbonyl)-amino]-benzoate (Compound A, 113 mg, 0.26 mmol) in 6 ml of methanol and 3 drops of conc. HCl was stirred at room temperature for overnight and then concentrated to dryness. The solid was recrystallized from ethyl ether: hexane to give the title compound as a white solid.

$^1$H NMR acetone-d$_6$ δ 10.2 (bs, 1H), 7.94 (s, 1H), 7.56 (s, 1H), 7.53 (s, 1H), 6.94 (s, 1H), 1.69 (s, 4H), 1.27 (s, 6H).

Ethyl 2,6-difluoro-4-[(3-hydroxy-5,5,8,8,-tetramethyl-5,6,7,8-tetrahydronaphthalene-2-carbonyl) -amino]-benzoate (Compound C)

To a solution of 2,6-difluoro-4-[(3-hydroxy-5,5,8,8,-tetramethyl-5,6,7,8 -tetrahydro-naphthalene-2-carbonyl)-amino]-benzoic acid (Compound B, 56 mg, 0.13 mmol) in 4 ml of acetone was added potassium carbonate (36 mg, 0.26 mmol) and iodoethane (0.012 ml, 0.14 mmol). The reaction mixture was stirred at room temperature for 4 hours then concentrated and purified by column chromatography with ethyl acetate: hexane (1:9) to yield the title compound as a white solid.

$^1$H NMR CDCl$_3$ δ 8.00 (s, 1H), 7.38 (s, 1H), 7.35 (s, 1H), 6.95 (s, 1H), 4.40 (q, J=7.1 Hz, 2H), 1.70 (s, 4H), 1.41 (t, J=7.2 Hz, 3H), 1.31 (s, 3H), 1.29 (s, 3H).

Ethyl 2,6-difluoro-4-[(3-hydroxy-4-chloro-5,5,8,8-tetramethyl-5,6,7,8-tetrahydro-naphthalene-2-carbonyl)-amino]-benzoate (Compound 1)

To a solution ethyl 2,6-difluoro-4-[(3-hydroxy-5,5,8,8-tetramethyl-5,6,7,8-tetrahydro-naphthalene-2-carbonyl)-amino]-benzoate (Compound C, 227 mg, 0.52 mmol) in 10 ml of anhydrous dichloromethane under nitrogen at 25° C. was added sulfuryl chloride (0.0413 ml, 0.57 mmol) and anhydrous ethyl ether (0.054 ml, 0.52 mmol). Reaction was instantaneous at 25° C. as monitored by $^1$H NMR. The reaction mixture was quenched with saturated NaHCO$_3$ then extracted with ethyl acetate. The organic layer was washed with water, brine and dried over Na$_2$SO$_4$. The title compound was obtained as a white solid after column chromatography with ethyl acetate:hexane (1:9).

$^1$H NMR CDCl$_3$ δ 9.33 (b, 1H), 8.56 (b, 1H), 7.90 (s, 1H), 7.36 (d, J=9.83 Hz, 2H), 4.39 (q, J=7.1 Hz, 2H), 1.75 (m, 2H), 1.65 (m, 2H), 1.53 (s, 6H), 1.39 (t, J=7.2 Hz, 3H), 1.32 (s, 6H).

2,6-Difluoro-4-[(3-hydroxy-4-chloro-5,5,8 8-tetramethyl-5,6,7,8-tetrahydronaphthalene-2-carbonyl) -amino]-benzoic acid (Compound 2)

To a solution of ethyl 4-[(4-chloro-3-hydroxy-5,5,8,8-tetramethyl-5,6,7,8-tetrahydro-naphthalene-2-carbonyl)-amino]-2,6-difluoro-benzoate (Compound 1, 150 mg, 0.32 mmol) in 6 ml of EtOH was added 2 ml of 2M NaOH(aq). The reaction was stirred at room temperature for 12 hours then acidified with 10% HCl to PH=5. The excess alcohol was removed by evaporation in a rotary apparatus and the aqueous layer was extracted with ethyl acetate (3×10 ml). The combined organic layers were washed with water, brine, and dried over Na$_2$SO$_4$. After evaporation of the solvent, the title compound was obtained in a crude form and was recrystallized in ethyl acetate/hexane to afford the pure title compound (AGN 195183) as a light yellow solid.

$^1$H NMR Acetone-d6 δ 7.97(s, 1H), 7.53(d, J=10.2 Hz, 2H), 1.75 (m, 2H), 1.65 (m, 2H), 1.54 (s, 6H), 1.31 (s, 6H).

Culture of Breast Cancer Cell Lines

The estrogen receptor-positive (ER$^+$) cell line T-47D and the ER$^-$-cell line SK-BR-3 were cultured in Dulbecco's modification of Eagle's medium (DMEM Gibco BRL, Gaithersburg, Md.) supplemented with 10% fetal bovine serum (HyClone, Logan, Utah), 2 mM L-glutamine and 1% antibiotics-antimycotics (Gibco BRL). Cell lines were obtained from the American Type Culture Collection (ATCC, Rockville, Md., HTB-133 and HTB-30 for T47-D and SKBR-3, respectively). Cells were cultured at 37° C. in a humidified atmosphere containing 5% CO$_2$.

Cell Proliferation Assay

Proliferation of cancer cell lines was determined using a commercial cell proliferation kit (Roche Diagnostics), essentially following the instructions of the manufacturer. Cells were seeded into 96-well tissue culture plates (Corning Incorporated, Corning, N.Y.) at a concentration of 3000 cells/well. After 24 hours, cells were treated with Compound 2 (AGN195183) and/or interferons (IFNs) or solvent alone. The appropriate concentrations of Compound 2 (AGN195183) used in this study were between $10^{-11}$M and $10^{-6}$M; IFNs concentrations were between 25 and 1000

Unit/ml. Culture media were changed every 72 hours. After 7days, 10 μl of 5-bromo-2'-deoxyuridine (BrdU) was added to each well. Incubation with BrdU was stopped 24 hours later by adding 100 μl of anti-BrdU antibody to each well. The amount of BrdU incorporated into the DNA of proliferating cells was assessed by measuring absorbance at 450 nm. Each experiment was performed in triplicate.

Criteria for Synergism

The growth inhibition observed in the cell cultures as a result of treatment with a combination of Compound 2 (AGN195183) of the invention and the interferons (IFNs) was analyzed for synergistic and additive effects. Synergistic effects were determined by calculating the ratio between the percentage of cell growth expected assuming an additive interaction and the actual cell growth observed when combining both agents (values >1 indicates synergistic actions). Statistical significance of synergistic effects were determined using two-sided student's t-test.

Synergism was defined as: %A×% B>%AB

Additivity was defined as: %A×%B=%AB where A and B are the effects of each individual agent and AB is the effect of the combination, in accordance with the teaching of Aapro et al., Cancer Chemother. Pharmacol., 10: 161 –166, 1983, and Marth et al., J. Natl. Cancer Inst., 77:1197–1202, 1986), both of which are expressly incorporated herein by reference.

Anti-Proliferative Effects Determined by the Assays

Referring now to the graphs of FIGS. 1 through 12, each of these represents the results obtained in the above described assays where SKBR-3 and T47-D cells, respectively, were treated with a combination of Compound 2 of the invention and human recombinant interferon (IFN) α, β, and γ, respectively. The graph of FIG. 13 illustrates the results of treatment of these two cell cultures only with Compound 2 of the invention, without the use of any other anti-tumor agent. In each of these graphs the incorporation of 5-bromo-2'-deoxyuridine (BrdU) is plotted on the Y (vertical) axis and varying concentration of Compound 2 of the invention or varying concentration of IFNα, IFNβ or of IFNγ, respectively is plotted on the X (horizontal) axis. The concentration of the interferons is expressed in international units, as is accepted in the art, whereas the molar concentration of Compound 2 is plotted on a logarithmic scale. Each graph, except for the graph of FIG. 13, includes a curve indicating results with one agent only, actual experimental results with the combination of the two agents (Compound 2 and the respective interferon), and a theoretical curve which is calculated in the manner described above, assuming for the calculation that the effects of the two agents would be simply additive. The incorporation of BrdU is plotted on a percentage basis relative to the situation when the agent of varying concentration in the respective graph was not used (0 concentration represents 100% incorporation).

Figure 1:
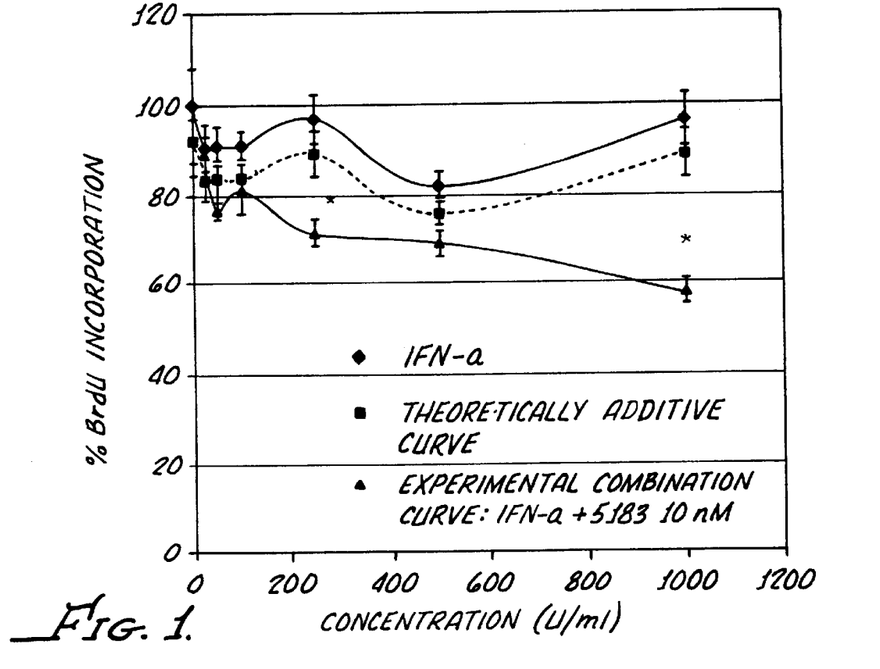
FIG. 1 is a graph showing synergism in the anti-proliferative effects of a combination of the compound AGN 195183 (Compound 2) of the invention and of α interferon (IFNα) in SKBR-3 cells.
Figure 2:
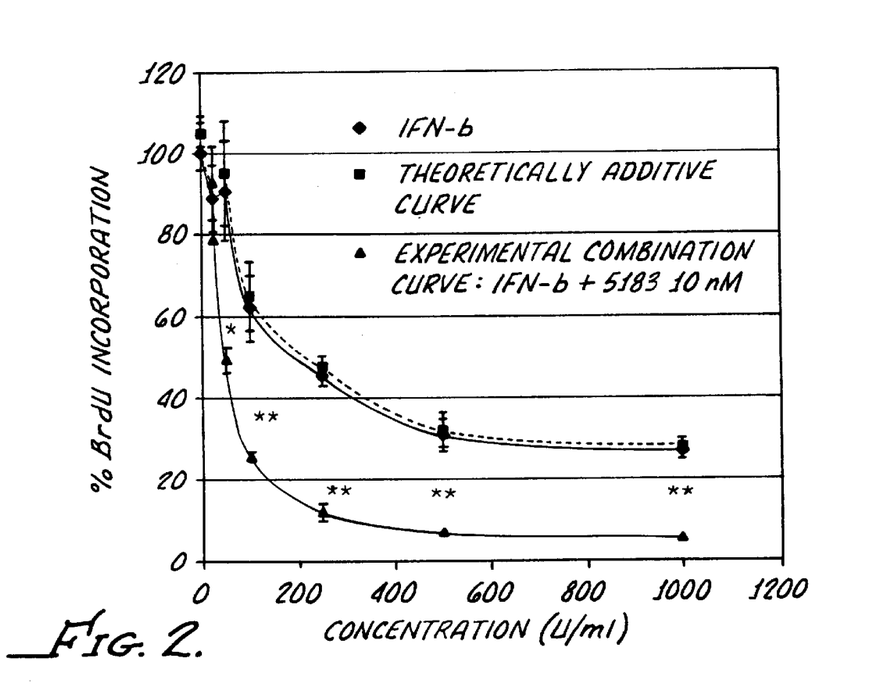
FIG. 2 is a graph showing synergism in the anti-proliferative effects of a combination of the compound AGN 195183 (Compound 2) of the invention and of β interferon (IFNβ) in SKBR-3 cells.
Figure 3:
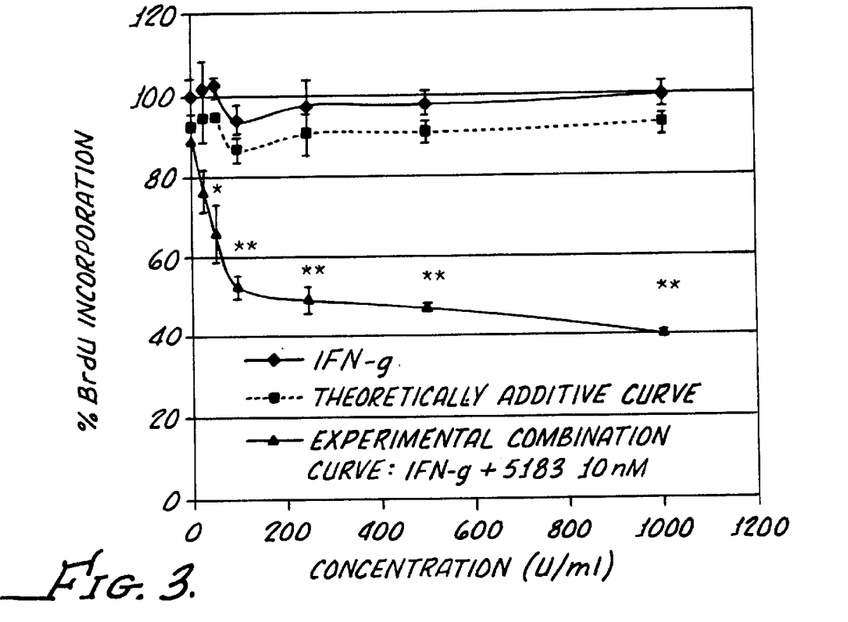
FIG. 3 is a graph showing synergism in the anti-proliferative effects of a combination of the compound AGN 195183 (Compound 2) of the invention and of γ interferon (IFNγ) in SKBR-3 cells.

Referring now specifically to the graph if FIG. 1, in the assay in SKBR-3 cells depicted in that graph the concentration of Compound 2 was 10 nanomolar (nM), and the concentration of the IFNα was varied. It can be seen on the graph that the experimentally or actually observed inhibition of cell proliferation was significantly greater (less BrdU incoproration) than with IFNα alone, and significantly greater than the theoretically additive curve, thus showing a synergistic effect of Compound 2 and IFNα. The graphs of FIGS. 2 and 3, similarly depict the results of assays in SKBR-3 cells where the concentration of Compound 2 was kept constant at 10 nM and the concentration of IFNβ or IFNγ, respectively, was varied. The graphs of FIGS. 2 and 3 also show significant synergistic effect of the combination treatment.

Figure 4:
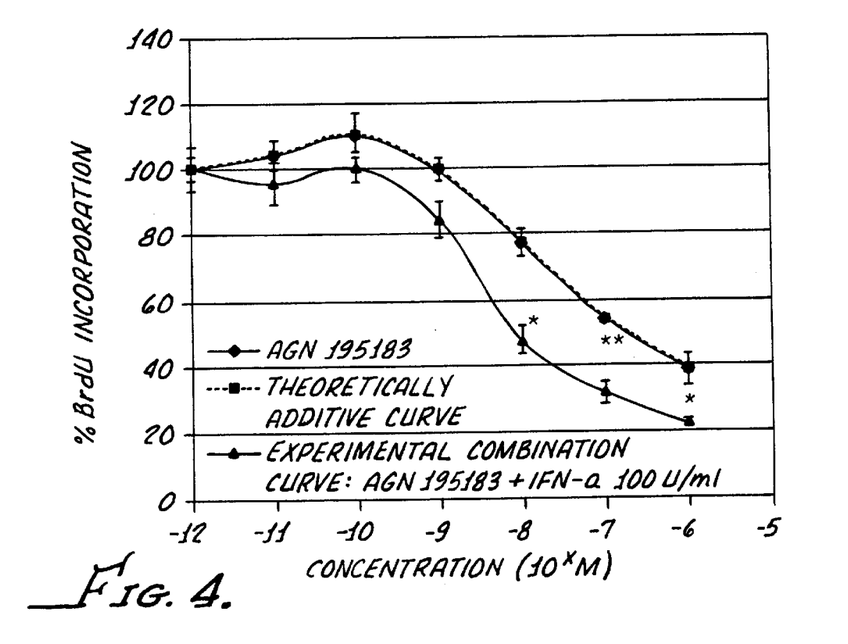
FIG. 4 is another graph showing synergism in the anti-proliferative effects of a combination of the compound AGN 195183 (Compound 2) of the invention and of α interferon (IFNα) in SKBR-3 cells.
Figure 5:
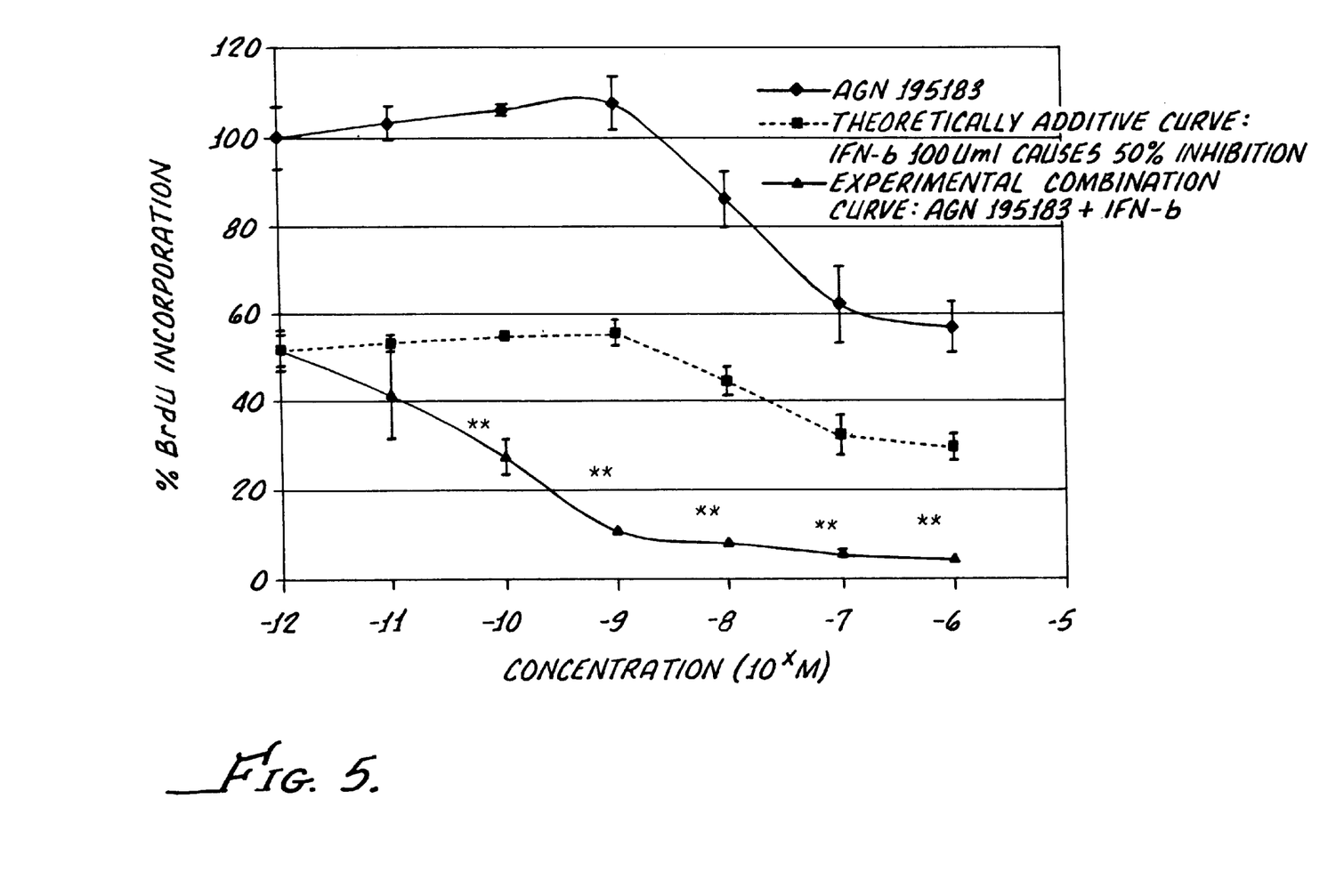
FIG. 5 is another graph showing synergism in the anti-proliferative effects of a combination of the compound AGN 195183 (Compound 2) of the invention and of β interferon (IFNβ) in SKBR-3 cells.
Figure 6:
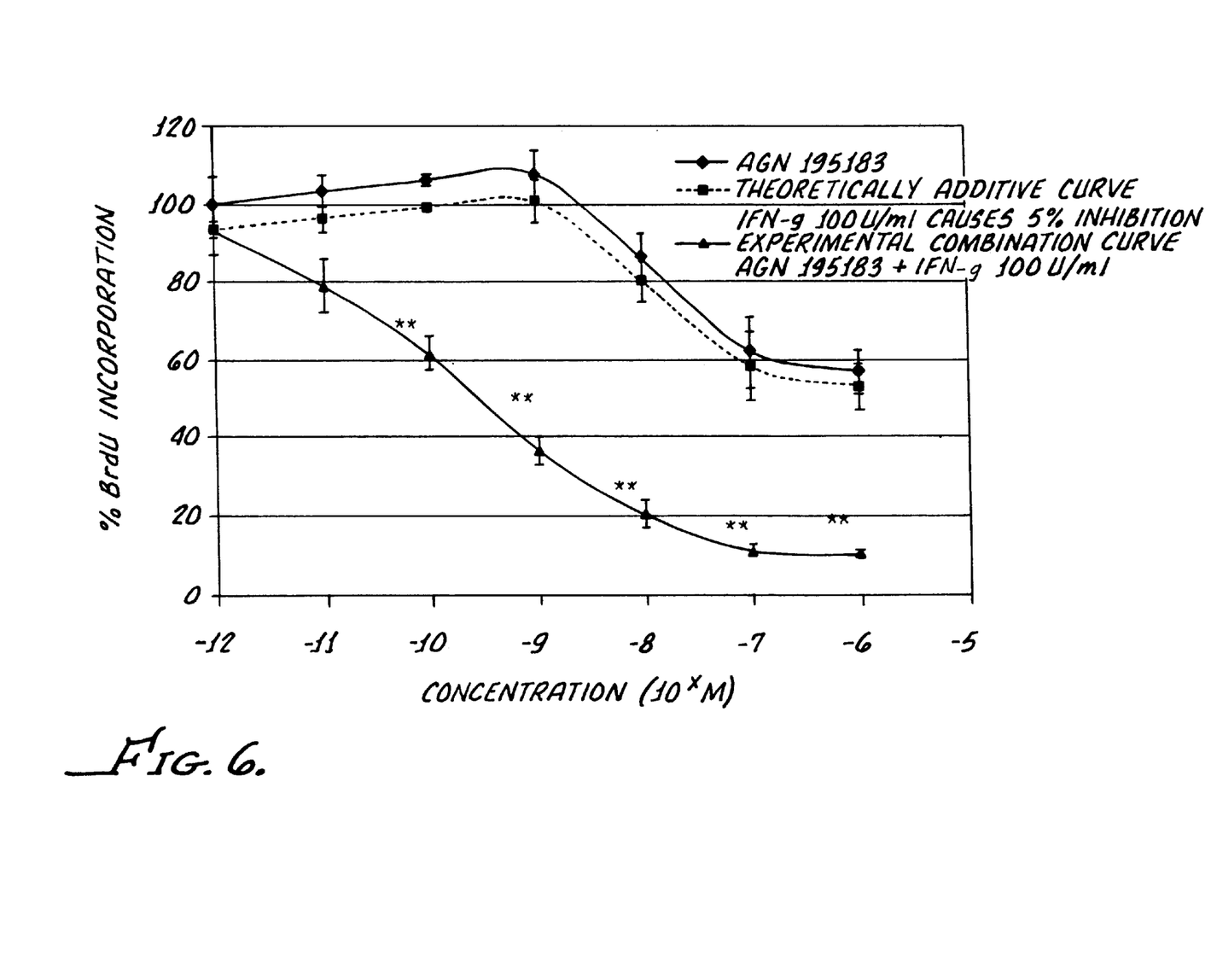
FIG. 6 is another graph showing synergism in the anti-proliferative effects of a combination of the compound AGN 195183 (Compound 2) of the invention and of γ interferon (IFNγ) in SKBR-3 cells.

The graphs of FIGS. 4, 5 and 6 disclose the results of assays in SKBR-3 cells where the concentration of IFNα, IFNβ and of IFNγ, respectively, was kept constant at 100 international units per ml (U/ml), and the concentration of Compound 2 of the invention was varied. These graphs also show significant synergistic effect, representing that the combination of the interferon and of Compound 2 inhibits cell proliferation significantly more than what would be expected based on the individual effects of these two agents.

Figure 7:
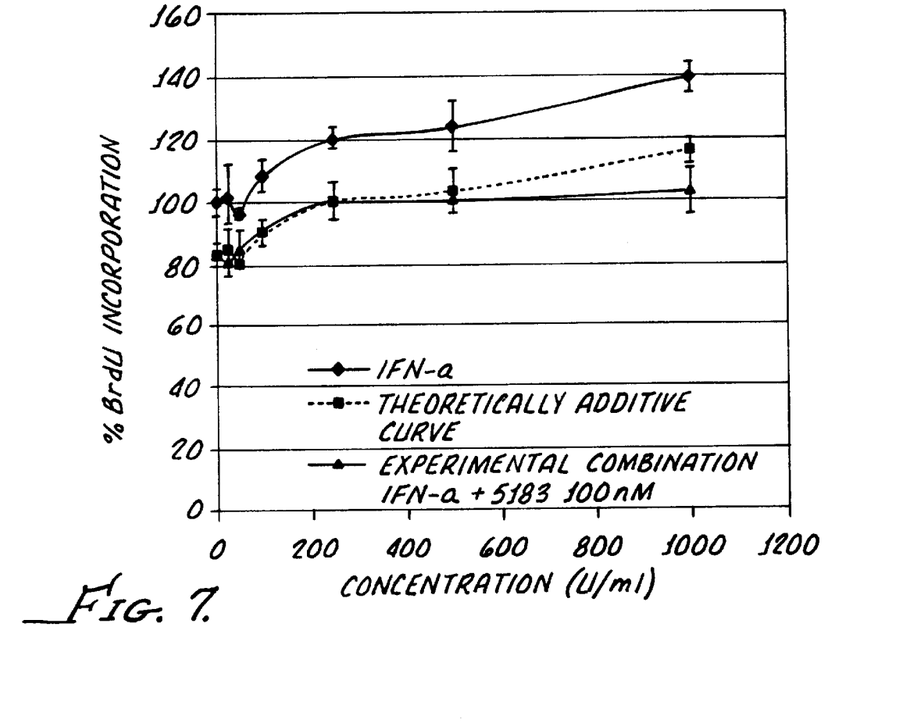
FIG. 7 is a graph showing the anti-proliferative effects of a combination of the compound AGN 195183 (Compound 2) of the invention and of α interferon (IFNα) in T47-D cells.
Figure 8:
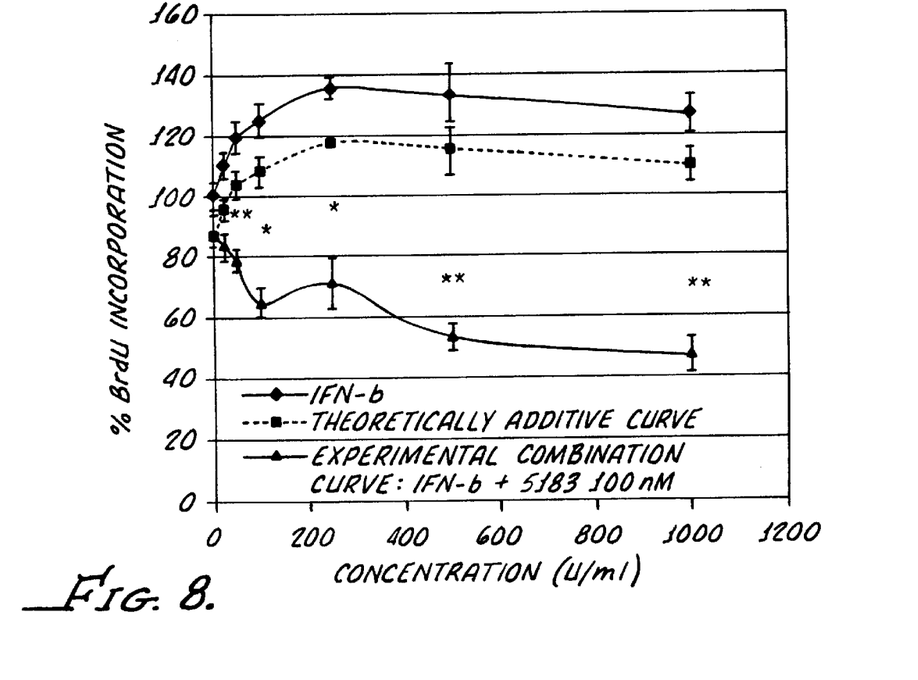
FIG. 8 is a graph showing synergism in the anti-proliferative effects of a combination of the compound AGN 195183 (Compound 2) of the invention and of β interferon (IFNβ) in T47-D cells.
Figure 9:
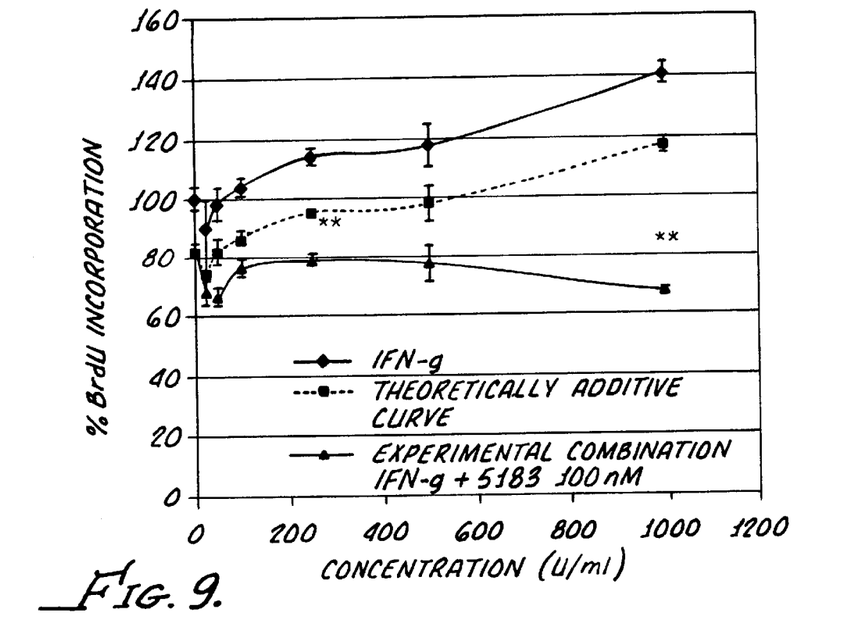
FIG. 9 is a graph showing synergism in the anti-proliferative effects of a combination of the compound AGN 195183 (Compound 2) of the invention and of γ interferon (IFNγ) in T47-D cells.

The graphs of FIGS. 7, 8 and 9 disclose results of assays in T47-D cells as a result of treatment with a combination of a constant concentration (100 nM) of Compound 2, and varying concentration of IFNα, IFNβ and of IFNγ, respectively. The graph of FIG. 7 reveals that inhibition by the combination is additive in this cell line when IFNα is used. However, when IFNβ and IFNγ were used, the observed inhibition was significantly synergistic.

Figure 10:
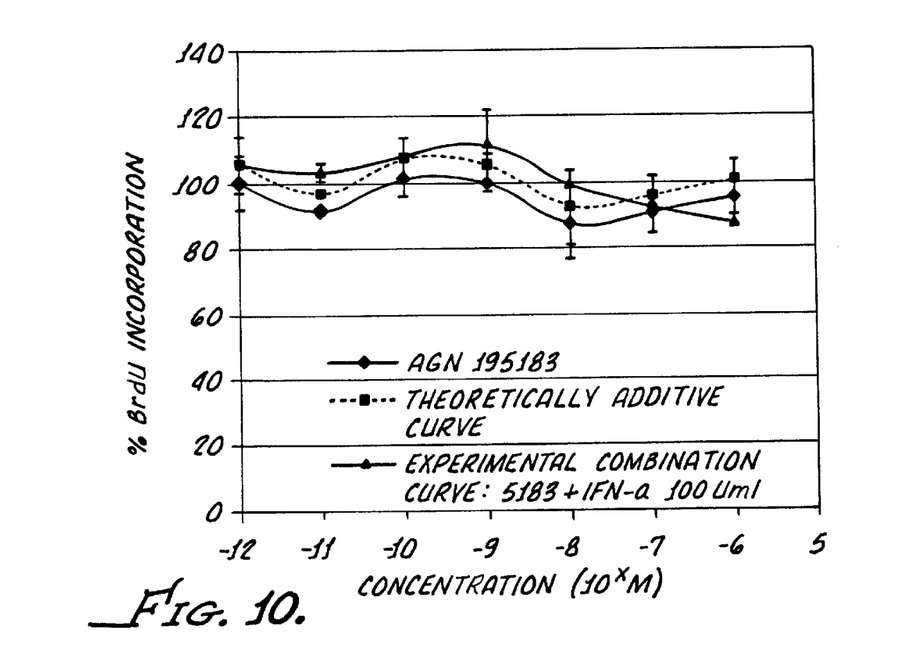
FIG. 10 is another graph showing the anti-proliferative effects of a combination of the compound AGN 195183 (Compound 2) of the invention and of α interferon (IFNα) in T47-D cells.
Figure 11:
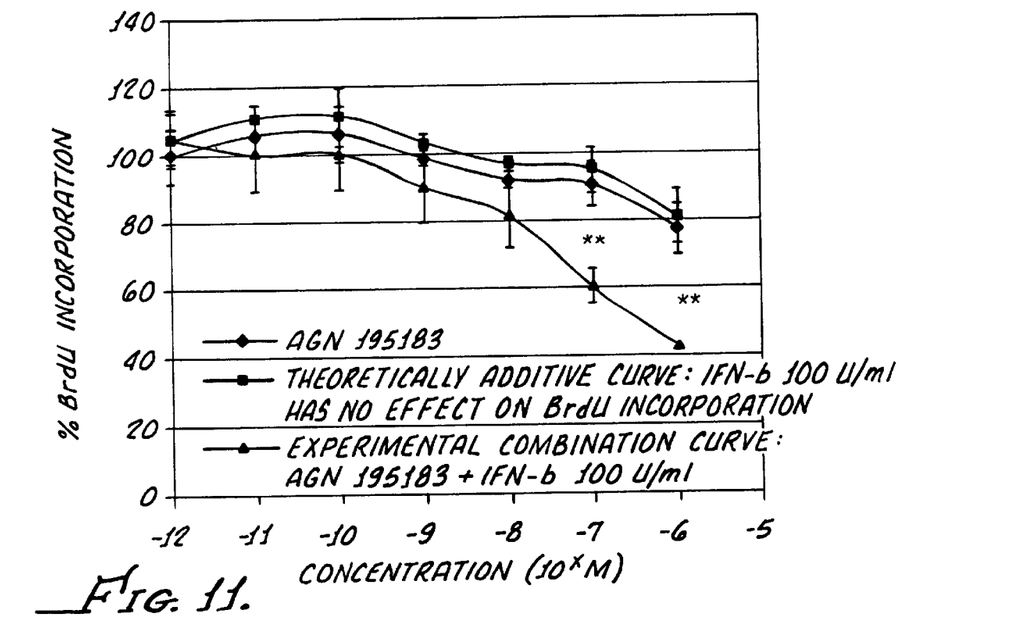
FIG. 11 is another graph showing synergism in the anti-proliferative effects of a combination of the compound AGN 195183 (Compound 2) of the invention and of β interferon (IFNβ) in T47-D cells.
Figure 12:
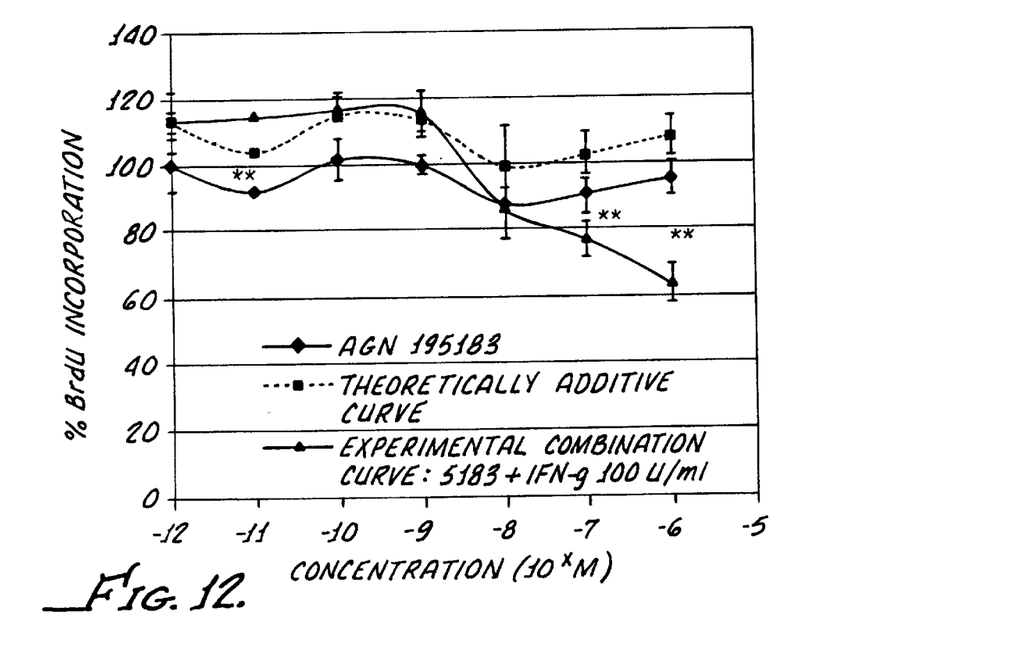
FIG. 12 is another graph showing synergism in the anti-proliferative effects of a combination of the compound AGN 195183 (Compound 2) of the invention and of γ interferon (IFNγ) in T47-D cells.
Figure 13:
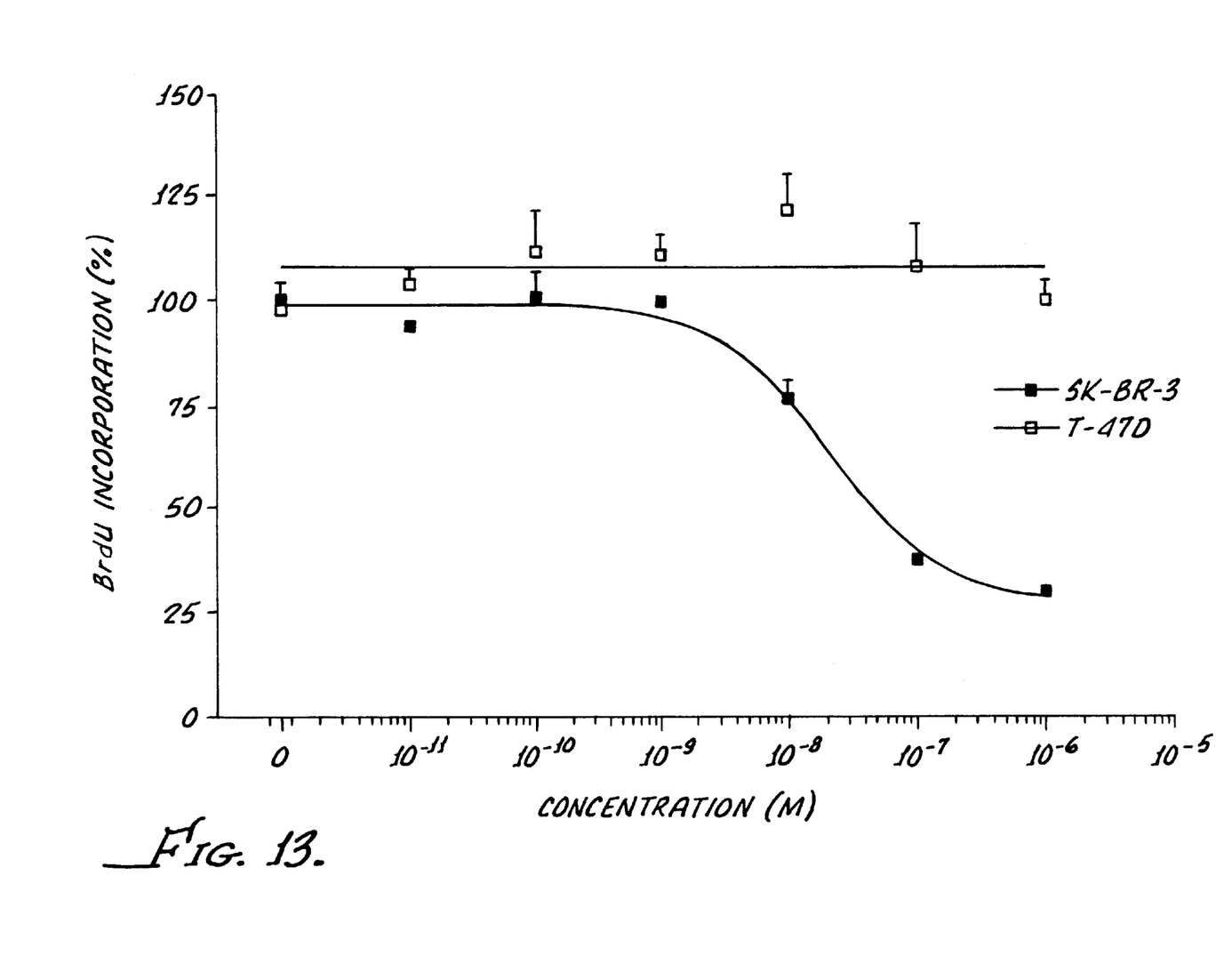
FIG. 13 is a graph showing the effect of compound AGN 195183 (Compound 2) of the invention in SKBR-3 and in T47-D cells.

FIGS. 10, 11 and 12 disclose the results of assays in T47-D cells where the concentration of IFNα, IFNβ and of IFNγ, respectively, was kept constant at 100 international units per ml (U/ml), and the concentration of Compound 2 of the invention was varied. When IFNα was used in the combination (FIG. 10) the combination was not very effective and merely additive, but when IFNβ and IFNγ were used, again synergistic inhibition was observed, in the cotreatment with IFNγ only at higher concentrations of Compound 2.

The foregoing results and particularly the synergism in the anti-proliferative effects on these two cancer cell lines of the compounds of the invention and of human recombinant interferon is unexpected, surprising, and an indication that RARα specific or RARα selective compounds, and particularly the preferred compounds of the invention are useful for the treatment of diseases involving malignant cell-proliferation, such as carcinomas and particularly carcinoma of the breast. In fact, the foregoing assays indicated that RARα specific or RARα selective compounds, and particularly the preferred compounds of the invention are useful in combination therapy with interferon in breast cancer cell lines which are estrogen receptor positive (T-47D) and also in human breast cancer cell lines which are estrogen receptor negative (SK-BR-3).

Methods of Treatment, Modes of Administration

The RARα specific or RARα selective compounds, and particularly the preferred compounds may be administered, in accordance with the present invention, systemically or topically, depending on such considerations as the condition to be treated, need for site-specific treatment, quantity of drug to be administered, and numerous other considerations. For the treatment of breast cancer and many other forms of malignant tumors the compounds are more likely to be administered systemically, in a pharmaceutical composition containing such excipients or inert components which are well known in the art pertaining to chemotherapy of tumors. More specifically, if the compound is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain other cases, it may be useful to formulate these compounds in suppository form or as extended release formulation for deposit under the skin or intramuscular injection.

The RARα specific or RARα selective compounds, and particularly the preferred compound of the invention will be administered as a chemotherapeutic agent for treatment of tumors in a useful therapeutic dose which will vary from condition to condition and in certain instances may vary with the severity of the condition being treated and the patient's susceptibility to treatment. Accordingly, no single dose will be uniformly useful, but will require modification depending on the particularities of the tumor or malignancy being treated. Such doses can be arrived at through routine experimentation. For the treatment of solid tumors, particularly breast cancer it is anticipated that the compound will be administered for approximately 1 to 8 weeks to a patient in need thereof, in a dose that is effective to halt, slow the growth or dissipate the tumor. Preferably the compound is to be administered orally, in a daily dose which preferably will be in the range of a approximately 50 mg per day to 500 mg per day. Most preferably the compound used in the treatment will be Compound 2 of the invention.

Preferably the RARα specific or RARα selective compounds, and particularly the preferred compounds of the invention, and most preferably Compound 2, will be administered, in accordance with the invention, in combination with other chemotherapeutic agents, such as interferons, preferably human recombinant interferon, or other known chemotherapeutic agents of tumors. Other chemotherapeutic agents with which the compounds are likely to be used in combination therapy are: tamixofen and taxol. With the use of interferons and with certain other chemotherapeutic agents as well, a synergistic anti-tumor effect is likely to occur, as is demonstrated by the above described cell culture assay procedures. Again, when the compounds are used in a combination therapy the useful therapeutic dose will vary from condition to condition and in certain instances may vary with the severity of the condition being treated and the patient's susceptibility to treatment. Accordingly, the required dose will be arrived at through routine experimentation, which is customary in the science of chemotherapy of tumors.

Generally speaking it is contemplated that in combination therapy and for the treatment of solid tumors such as breast cancer, the daily dose of the compound will be in the range of a approximately 50 mg per day to 500 mg per day. The daily dose of the other chemotherapeutic agent or agents given in combination with the compound of the invention will depend on the nature of the chemotherapeutic agent or agents, and can be arrived by routine experimentation normally practiced in the art. When interferon is used for the treatment of solid tumors, such as for example breast cancer, in combination with RARα specific or RARα selective compounds, and particularly with the preferred the compounds of the invention, then the daily dose of the interferon is likely to be in the range of approximately 1 to 9 million international units per day.

What is claimed is:

1. A compound of the formula wherein R is a H, lower alkyl of 1 to 6 carbons, or a pharmaceutically acceptable salt of said compound.

2. A compound in accordance with claim 1 wherein R is lower alkyl of 1 to 3 carbons.

3. A compound in accordance with claim 1 wherein R is H, or a pharmaceutically acceptable salt of said compound.

4. A pharmaceutical composition for the treatment of a malignant disease or condition in a mammal, the composition comprising a pharmaceutically acceptable excipient and a therapeutically effective dose of a compound of the formula wherein R is a H, lower alkyl of 1 to 6 carbons, or a pharmaceutically acceptable salt of said compound.

5. A pharmaceutical composition in accordance with claim 4 wherein in the formula of the compound R is lower alkyl of 1 to 3 carbons.

6. A pharmaceutical composition in accordance with claim 4 wherein in the formula of the compound R is is H, or a pharmaceutically acceptable salt of said compound.

7. A pharmaceutical composition in accordance with claim 4 further comprising a chemotherapeutic agent effective for the treatment of the malignant disease or condition of the mammal.

8. A pharmaceutical composition in accordance with claim 5 further comprising a chemotherapeutic agent effective for the treatment of the malignant disease or condition of the mammal.

9. A pharmaceutical composition in accordance with claim 6 further comprising a chemotherapeutic agent effective for the treatment of the malignant disease or condition of the mammal.

10. A pharmaceutical composition in accordance with claim 7 wherein the chemotherapeutic agent effective for the treatment of the malignant disease or condition of the mammal is interferon.

11. A pharmaceutical composition in accordance with claim 8 wherein the chemotherapeutic agent effective for the treatment of the malignant disease or condition of the mammal is interferon.

12. A pharmaceutical composition in accordance with claim 9 wherein the chemotherapeutic agent effective for the treatment of the malignant disease or condition of the mammal is interferon.

13. A pharmaceutical composition in accordance with claim 4 comprising a daily dose of approximately 50 mg to 500 mg of the compound.

14. A pharmaceutical composition in accordance with claim 4 adapted for the treatment of breast cancer.

15. A pharmaceutical composition in accordance with claim 9 wherein the chemotherapeutic agent effective for the treatment of the malignant disease or condition of the mammal is human recombinant interferon α, human recombinant interferon β, or human recombinant interferon γ.

16. A pharmaceutical composition in accordance with claim 15 adapted for the treatment of breast cancer.

17. A method of combination therapy for treating a malignant disease or condition in a mammal in need of such treatment, the method comprising the steps of administering to the mammal a pharmaceutical composition comprising a pharmaceutically acceptable excipient and a therapeutically effective dose of a compound of the formula wherein R is a H, lower alkyl of 1 to 6 carbons, or a pharmaceutically acceptable salt of said compound, and co-administering to the mammal another chemotherapeutic agent effective for the treatment of the malignant disease or condition of the mammal.

18. A method in accordance with claim 17 wherein in the formula of the compound R is lower alkyl of 1 to 3 carbons.

19. A method in accordance with claim 17 wherein in the formula of the compound R is H, or a pharmaceutically acceptable salt of said compound.

20. A method in accordance with claim 17 wherein a daily dose of approximately 50 mg to 500 mg of the compound is administered to the mammal.

21. A method in accordance with claim 17 wherein the malignant disease or condition of the mammal is breast cancer.

22. A method in accordance with claim 17 wherein the other chemotherapeutic agent is interferon.

23. A method in accordance with claim 21 wherein the other chemotherapeutic agent is interferon.

24. A method of combination therapy for treating a malignant disease or condition in a mammal in need of such treatment, the method comprising the steps of administering to the mammal a pharmaceutical composition comprising a pharmaceutically acceptable excipient and a therapeutically effective dose of a compound that is specific or seletive agonist of RARα receptors in preference over RARβ and RARγ receptors, and co-administering to the mammal another chemotherapeutic agent effective for the treatment of the malignant disease or condition of the mammal.

25. A method in accordance with claim 24 wherein a daily dose of approximately 50 mg to 500 mg of the RARα specific or selective compound is administered to the mammal.

26. A method in accordance with claim 24 wherein the malignant disease or condition of the mammal is breast cancer.

27. A method in accordance with claim 24 wherein the other chemotherapeutic agent is interferon.

28. A method in accordance with claim 24 wherein the malignant disease or condition of the mammal is breast cancer, the other chemotherapeutic agent is interferon and a daily dose of approximately 50 mg to 500 mg of the RARα specific or selective compound is administered to the mammal.

* * * * *

UNITED STATES PATENT AND TRADEMARK OFFICE
CERTIFICATE OF CORRECTION

PATENT NO.   : 6,387,950 B2
DATED        : May 14, 2002
INVENTOR(S)  : Nehme et al.

It is certified that error appears in the above-identified patent and that said Letters Patent is hereby corrected as shown below:

Column 8,
Line 27, "C." should be -- C --.

Column 10,
Line 15, "C." should be -- C --.
Line 18, "C." should be -- C --.
Line 28, "5,5,8 8" should be -- 5,5,8,8 --.

Signed and Sealed this

Twenty-second Day of April, 2003

JAMES E. ROGAN
*Director of the United States Patent and Trademark Office*